(12) United States Patent
O'Farrell et al.

(10) Patent No.: US 8,425,569 B2
(45) Date of Patent: Apr. 23, 2013

(54) IMPLANTABLE VERTEBRAL FRAME SYSTEMS AND RELATED METHODS FOR SPINAL REPAIR

(75) Inventors: Desmond O'Farrell, Grand Rapids, MI (US); Andrew J. Rodenhouse, Grand Rapids, MI (US); Mark E. Zyzelewski, Kalamazoo, MI (US)

(73) Assignee: TransCorp, Inc., Ada, MI (US)

( * ) Notice: Subject to any disclaimer, the term of this patent is extended or adjusted under 35 U.S.C. 154(b) by 125 days.

(21) Appl. No.: 12/783,499

(22) Filed: May 19, 2010

(65) Prior Publication Data
US 2011/0288590 A1 Nov. 24, 2011

(51) Int. Cl.
*A61B 17/70* (2006.01)
*A61B 17/88* (2006.01)

(52) U.S. Cl.
USPC ......... 606/279; 606/280; 606/281; 623/17.16

(58) Field of Classification Search .................. 606/280, 606/281, 289, 295, 296; 623/17.11, 17.16
See application file for complete search history.

(56) References Cited

U.S. PATENT DOCUMENTS

| | | | |
|---|---|---|---|
| 3,741,205 A | 6/1973 | Markolf et al. |
| 5,059,194 A | 10/1991 | Michelson |
| 5,246,458 A | 9/1993 | Graham |
| 5,306,275 A | 4/1994 | Bryan |
| 5,423,826 A | 6/1995 | Coates et al. |
| 5,486,180 A | 1/1996 | Dietz et al. |

(Continued)

FOREIGN PATENT DOCUMENTS

| | | |
|---|---|---|
| DE | 4434384 A1 | 3/1996 |
| DE | 10307758 A | 9/2004 |

(Continued)

OTHER PUBLICATIONS

Choi et al.; Modified transcorporeal anterior cervical microforaminotomy for cervical radiculopathy: a technical note and early results; Eur. Spine. J.; vol. 16; pp. 1387-1393; 2007.

(Continued)

*Primary Examiner* — Kevin T Truong
*Assistant Examiner* — Christian Sevilla
(74) *Attorney, Agent, or Firm* — Shay Glenn LLP

(57) ABSTRACT

The invention relates generally to systems and methods for securing adjacent vertebrae in a fixed spacial relationship. In one embodiment, the system includes at least one interbody repair implant, at least one implantable vertebral frame and at least one retention member. In this embodiment, the interbody repair implant is sized to fit in an intervertebral space. The at least one implantable vertebral frame is configured to span between the adjacent vertebrae. The frame is also configured to attach to each of the adjacent vertebra to postoperatively maintain a desired spatial relationship between the vertebrae. The frame has at least one internal aperture therethrough for providing visual access to at least a portion of the interbody repair implant, both intra-operatively and post-operatively. Methods of fusing two or more adjacent vertebral bodies in a portion of a spinal column are also disclosed. One such method includes the steps of inserting an interbody repair implant into a intervertebral space, securing an implantable vertebral fixation frame to the adjacent vertebral bodies over the implant, installing a retention member to the frame to cover at least a portion of the aperture, and moving a locking portion of the retention member from an unlocked position to a locked position.

13 Claims, 16 Drawing Sheets

U.S. PATENT DOCUMENTS

| | | | |
|---|---|---|---|
| 5,489,307 A | 2/1996 | Kuslich et al. | |
| 5,505,732 A | 4/1996 | Michelson | |
| 5,645,599 A | 7/1997 | Samani | |
| 5,722,977 A | 3/1998 | Wilhelmy | |
| 5,741,253 A | 4/1998 | Michelson | |
| 5,766,253 A | 6/1998 | Brosnahan, III | |
| 5,772,661 A | 6/1998 | Michelson | |
| 5,795,291 A | 8/1998 | Koros | |
| 5,797,909 A | 8/1998 | Michelson | |
| 5,800,433 A | 9/1998 | Benzel et al. | |
| 5,851,207 A | 12/1998 | Cesarone | |
| 5,893,890 A | 4/1999 | Pisharodi | |
| 5,984,922 A | 11/1999 | McKay | |
| 6,056,749 A | 5/2000 | Kuslich | |
| 6,066,142 A | 5/2000 | Serbousek | |
| 6,080,155 A | 6/2000 | Michelson | |
| 6,096,038 A | 8/2000 | Michelson | |
| 6,102,950 A | 8/2000 | Vaccaro | |
| 6,159,214 A | 12/2000 | Michelson | |
| 6,193,721 B1 | 2/2001 | Michelson | |
| 6,207,498 B1 | 3/2001 | Chen et al. | |
| 6,224,599 B1 | 5/2001 | Baynham et al. | |
| 6,224,607 B1 | 5/2001 | Michelson | |
| 6,231,610 B1 | 5/2001 | Geisler | |
| 6,241,733 B1 | 6/2001 | Nicholson et al. | |
| 6,258,094 B1 | 7/2001 | Nicholson et al. | |
| 6,261,293 B1 | 7/2001 | Nicholson et al. | |
| 6,287,313 B1 | 9/2001 | Sasso | |
| 6,315,795 B1 | 11/2001 | Scarborough et al. | |
| 6,332,887 B1 | 12/2001 | Knox et al. | |
| 6,342,056 B1 | 1/2002 | Mac-Thiong et al. | |
| 6,348,058 B1 | 2/2002 | Melkent et al. | |
| 6,371,986 B1 | 4/2002 | Bagby | |
| 6,383,186 B1 | 5/2002 | Michelson | |
| 6,385,475 B1 | 5/2002 | Cinquin et al. | |
| 6,413,259 B1 | 7/2002 | Lyons et al. | |
| 6,440,139 B2 | 8/2002 | Michelson | |
| 6,447,544 B1 | 9/2002 | Michelson | |
| 6,461,359 B1 | 10/2002 | Tribus et al. | |
| 6,517,544 B1 | 2/2003 | Michelson | |
| 6,558,390 B2 | 5/2003 | Cragg | |
| 6,562,046 B2 | 5/2003 | Sasso | |
| 6,562,074 B2 | 5/2003 | Gerbec et al. | |
| 6,572,619 B2 | 6/2003 | Santilli | |
| 6,579,290 B1 | 6/2003 | Hardcastle et al. | |
| 6,599,292 B1 | 7/2003 | Ray | |
| 6,607,530 B1 | 8/2003 | Carl et al. | |
| 6,648,917 B2 | 11/2003 | Gerbec et al. | |
| 6,663,637 B2 | 12/2003 | Dixon et al. | |
| 6,709,438 B2 | 3/2004 | Dixon et al. | |
| 6,770,074 B2 | 8/2004 | Michelson | |
| 6,837,905 B1 | 1/2005 | Lieberman | |
| 6,859,661 B2 | 2/2005 | Tuke | |
| 6,923,811 B1 | 8/2005 | Carl et al. | |
| 7,014,633 B2 | 3/2006 | Cragg | |
| 7,033,362 B2 | 4/2006 | McGahan et al. | |
| 7,081,119 B2 | 7/2006 | Stihl | |
| 7,083,623 B2 | 8/2006 | Michelson | |
| 7,153,304 B2 | 12/2006 | Robie et al. | |
| 7,163,542 B2 | 1/2007 | Ryan | |
| 7,179,225 B2 | 2/2007 | Shluzas et al. | |
| 7,207,991 B2 | 4/2007 | Michelson | |
| 7,303,565 B2 | 12/2007 | Buttermann et al. | |
| 7,527,641 B2* | 5/2009 | Suh | 606/289 |
| 7,837,735 B2 | 11/2010 | Malone | |
| 2001/0047172 A1 | 11/2001 | Foley et al. | |
| 2002/0058944 A1 | 5/2002 | Michelson | |
| 2003/0055427 A1 | 3/2003 | Graf | |
| 2003/0060825 A1 | 3/2003 | Alfaro et al. | |
| 2003/0060828 A1 | 3/2003 | Michelson | |
| 2003/0065329 A1 | 4/2003 | Vaughan | |
| 2003/0083667 A1 | 5/2003 | Ralph et al. | |
| 2003/0149341 A1 | 8/2003 | Clifton | |
| 2003/0149434 A1 | 8/2003 | Paul | |
| 2003/0187441 A1 | 10/2003 | Bolger et al. | |
| 2003/0236526 A1 | 12/2003 | Van Hoeck et al. | |
| 2003/0236528 A1* | 12/2003 | Thramann | 606/99 |
| 2004/0006343 A1 | 1/2004 | Sevrain | |
| 2004/0097925 A1 | 5/2004 | Boehm et al. | |
| 2004/0106924 A1 | 6/2004 | Ralph et al. | |
| 2004/0106927 A1 | 6/2004 | Ruffner et al. | |
| 2004/0106997 A1 | 6/2004 | Lieberson | |
| 2004/0153089 A1 | 8/2004 | Zdeblick et al. | |
| 2004/0181223 A1* | 9/2004 | Ritland | 606/61 |
| 2004/0204717 A1 | 10/2004 | Fanger et al. | |
| 2004/0215203 A1 | 10/2004 | Michelson | |
| 2004/0267274 A1 | 12/2004 | Patel et al. | |
| 2005/0027293 A1 | 2/2005 | LeHuec et al. | |
| 2005/0043738 A1 | 2/2005 | Ryan | |
| 2005/0043740 A1 | 2/2005 | Haid et al. | |
| 2005/0137597 A1 | 6/2005 | Butler et al. | |
| 2005/0149026 A1 | 7/2005 | Butler et al. | |
| 2005/0149046 A1 | 7/2005 | Friedman et al. | |
| 2005/0267481 A1 | 12/2005 | Carl et al. | |
| 2006/0030858 A1 | 2/2006 | Simonson et al. | |
| 2006/0036247 A1 | 2/2006 | Michelson | |
| 2006/0074424 A1 | 4/2006 | Alleyne et al. | |
| 2006/0084844 A1 | 4/2006 | Nehls | |
| 2006/0094951 A1 | 5/2006 | Dean et al. | |
| 2006/0122605 A1* | 6/2006 | Suh et al. | 606/69 |
| 2006/0122701 A1 | 6/2006 | Kiester | |
| 2006/0122704 A1 | 6/2006 | Vresilovic et al. | |
| 2006/0136058 A1 | 6/2006 | Pietrzak | |
| 2006/0149251 A1 | 7/2006 | Ziolo et al. | |
| 2006/0167457 A1 | 7/2006 | Suddaby | |
| 2006/0235398 A1 | 10/2006 | Farris et al. | |
| 2006/0241646 A1 | 10/2006 | Stihl | |
| 2006/0247630 A1 | 11/2006 | Iott et al. | |
| 2006/0247654 A1 | 11/2006 | Berry | |
| 2006/0271198 A1 | 11/2006 | McAfee | |
| 2006/0276794 A1 | 12/2006 | Stern | |
| 2007/0043369 A1 | 2/2007 | Wallenstein et al. | |
| 2007/0168043 A1 | 7/2007 | Ferree | |
| 2007/0173842 A1 | 7/2007 | Abdou | |
| 2007/0203500 A1 | 8/2007 | Gordon et al. | |
| 2007/0233107 A1 | 10/2007 | Zielinski | |
| 2007/0233260 A1 | 10/2007 | Cragg | |
| 2007/0270851 A1* | 11/2007 | Erickson et al. | 606/69 |
| 2008/0039847 A1 | 2/2008 | Piper et al. | |
| 2008/0045966 A1 | 2/2008 | Buttermann et al. | |
| 2008/0077152 A1 | 3/2008 | McClintock et al. | |
| 2008/0269806 A1 | 10/2008 | Zhang et al. | |
| 2009/0043340 A1* | 2/2009 | Lowry et al. | 606/280 |
| 2009/0076516 A1 | 3/2009 | Lowry et al. | |
| 2009/0076555 A1 | 3/2009 | Lowry et al. | |
| 2009/0088604 A1 | 4/2009 | Lowry et al. | |
| 2009/0099568 A1 | 4/2009 | Lowry et al. | |
| 2009/0143716 A1 | 6/2009 | Lowry et al. | |
| 2009/0171396 A1 | 7/2009 | Baynham et al. | |
| 2009/0187191 A1 | 7/2009 | Carl et al. | |
| 2010/0057134 A1 | 3/2010 | Lowry et al. | |
| 2010/0152784 A1 | 6/2010 | Lowry et al. | |
| 2010/0152793 A1 | 6/2010 | Lowry et al. | |
| 2012/0209387 A1 | 8/2012 | Lowry et al. | |

FOREIGN PATENT DOCUMENTS

| | | |
|---|---|---|
| EP | 0890341 A1 | 1/1999 |
| FR | 2727005 A1 | 5/1996 |
| SU | 1424826 A1 | 9/1988 |
| WO | WO97/06753 A2 | 2/1997 |
| WO | WO98/14142 A1 | 4/1998 |
| WO | WO02/09626 A1 | 2/2002 |
| WO | WO02/069811 | 9/2002 |
| WO | WO 02/080789 A1 | 10/2002 |
| WO | WO03/075774 A1 | 9/2003 |
| WO | WO 2005/039651 A2 | 5/2005 |
| WO | WO2006/058079 A2 | 6/2006 |
| WO | WO2007/002251 | 1/2007 |
| WO | WO2007/018458 A1 | 2/2007 |
| WO | WO2007/089858 A2 | 8/2007 |

OTHER PUBLICATIONS

George et al.; Oblique transcorporeal approach to anteriorly located lesions in the cervical spinal canal; Acta. Neurochir. (Wien); vol. 121; pp. 187-190; 1993.

George et al.; Oblique transcorporeal drilling to treat anterior compression of the spinal cord at the cervical level; Minim. Invas. Neurosurg.; vol. 37; pp. 48-52; 1994.

Hong et al.; Comparison between transuncal approach and upper vertebral transcorporeal approach for unilateral cervical radiculopathy—a preliminary report; Minim. Invas. Neurosurg.; vol. 49; pp. 296-301; 2006.

Jho et al.; Ventral uncoforaminotomy; J. Neurosurg. Spine; vol. 7; pp. 533-536; 2007.

Jho et al.; Anterior microforaminotomy for treatment of cervical radiculopathy: part 1—disc-preserving functional cervical disc surgery; Neurosurgery; vol. 51; supp. 2; pp. S-46-53; Nov. 2002.

Kim et al.; Anterior decompression via a wide transvertebral approach and a ceramic insert in a patient with cervical degenerative disease; Surgical neurology; vol. 67; pp. 127-134; 2007.

Wolf et al.; MBARS: mini bone-attached robotic system for joint arthroplasty; Int. J. Medical Robotics and Computer Assisted Surgery; vol. 1; No. 2; pp. 101-121; 2005.

* cited by examiner

IMPLANTABLE VERTEBRAL FRAME SYSTEMS AND RELATED METHODS FOR SPINAL REPAIR

CROSS-REFERENCE TO RELATED APPLICATIONS

This application is related to U.S. patent application Ser. No. 12/616,762 entitled "Implantable Vertebral Frame Systems and Related Methods for Spinal Repair", filed Nov. 11, 2009, which is a continuation-in-part of U.S. patent application Ser. No. 11/855,124 entitled "Implantable Bone Plate System and Related Method for Spinal Repair", filed Sep. 13, 2007, which claims priority to U.S. Provisional Patent Application Ser. No. 60/954,511 entitled "Implantable Bone Plate System and Related Method for Spinal Repair", filed Aug. 7, 2007. Each patent application is incorporated herein by reference in its entirety.

The present invention relates to a system for performing surgical repair of the spine, such as for but not limited to the delivery of an interbody repair device for the purpose of either fusion or dynamic stabilization.

BACKGROUND

It is current practice in spinal surgery to use bone fixation devices to improve the mechanical stability of the spinal column and to promote the proper healing of injured, damaged or diseased spinal structures. Typically, corrective surgery entails the removal of damaged or diseased tissue, a decompression of one or more neural elements, followed by the insertion of an intervertebral implant for the purposes of a fusion or disc arthroplasty. In cases where spinal fusion is the desired surgical outcome, the final step is often to apply a bone plate in order to immobilize adjacent vertebral bones to expedite osteogenesis across said vertebral segments.

Most current surgical techniques require that damaged vertebral tissue be placed under rigid axial distraction throughout much of the procedure. This allows for greater ease in the removal of tissue, provides a larger working space for instrument maneuverability, enhances the surgeon's visibility and assists with the fit of the interbody implant once the distractor apparatus is removed. Conventional distraction of the spine typically employs the use of temporary "distractor pins" placed directly into the bone tissue adjacent to the disc space to be repaired, which are subsequently induced to move axially by the attachment and adjustment of a secondary tool. An alternative method employs the use of a ratcheting spreader device which is inserted directly into the vertebral interspace and is adjusted thereafter to achieve desired distraction.

In the conventional method, once the implant has been inserted, the distractor device is removed and the vertebrae can be secured by the attachment of a bone plate. Such bone plates, including a plurality of bone screws, are applied near the completion of the procedure to provide vertebral fixation and prohibit undesirable migration of the intervertebral implant.

Several design constructs have already been proposed in which a device is applied to adjacent vertebrae at the start of a procedure, prior to tissue removal, for the purposes of achieving and maintaining preferred vertebral alignment while serving also to constrain tissue removal throughout the procedure. The disclosed or published art in this method can generally be categorized into two broad categories: removable devices and permanently implantable devices.

The removable devices differ from the present proposed invention in that the devices used to maintain preferred vertebral alignment are temporary inserts and are subsequently removed after tissue removal so that a repair device may be delivered thereafter. The prior art which discloses permanently implantable devices differs in that the devices function solely to maintain preferred vertebral alignment and are not part of a comprehensive system and related method to precisely control and permanently maintain the preferred spatial relationship of adjacent vertebral members for controlled tissue removal and delivery of a repair device.

Removable Devices

U.S. Pat. No. 7,153,304 entitled Instrument System for Preparing a Disc Space Between Adjacent Vertebral Bodies to Receive a Repair Device, issued Dec. 26, 2006 to Robie et al., discloses a removable instrument system for preparing a disc space between adjacent vertebral bodies using a series of distractors that restore natural lordosis before a temporary template is attached for vertebral immobilization and to function as a guide for an insertable reamer meant for tissue removal.

U.S. Pat. No. 7,083,623 to Michelson, entitled Milling Instrumentation and Method for Preparing a Space Between Adjacent Vertebral Bodies, issued Aug. 1, 2006, discloses a removable milling device and method for preparing a space between adjacent vertebral bodies which essentially maintains preferred vertebral alignment while functioning as a saw guide to control bone and soft tissue removal.

US Pat. App. 2005/0043740 to Haid, entitled Technique and Instrumentation for Preparation of Vertebral Members, published Feb. 24, 2005, discloses a removable instrumentation set and technique for preparation of vertebral members utilizing a docking ring which is temporarily applied to the anterior spine to maintain preferred vertebral alignment and to function as a docking plate for an articulating bone removal device.

U.S. Pat. No. 7,033,362 to McGahan, entitled Instruments and Techniques for Disc Space Preparation, issued Apr. 25, 2006, discloses a removable instrumentation set and method for disc space preparation whereby an intervertebral device is temporarily inserted for the purpose of constraining tissue removal and guiding the position of an intervertebral repair device.

US Pat. App. 2003/0236526 to Van Hoeck, entitled Adjustable Surgical Guide and Method of Treating Vertebral Members, published Dec. 25, 2003, discloses a removable surgical guide and method with adjustable functionality for the preparation of adjacent vertebra.

US Pat. App. No. 2006/0247654 to Berry, entitled Instruments and Techniques for Spinal Disc Space Preparation, published Nov. 2, 2006, discloses a removable milling instrument assembly for vertebral endplate preparation which constrains a cutting path obliquely oriented to the axis of the vertebra.

Permanently Implanted Devices

US Pat. App. 2004/0097925 to Boehm, entitled Cervical Spine Stabilizing System and Method, published May 20, 2004, discloses a permanently implantable spine stabilizing system and method whereby a plate configured to be positively centered along the midline is placed to retain adjacent vertebra in a desired spatial relationship during discectomy and fusion procedures. The disclosed invention uses a series of temporary implants and removable drill templates in an attempt to assure the alignment of the implanted device along the midline of the spinal column. This alignment is typically not considered to be significant in determined the clinical outcome of the procedure and is further considered impractical for the purposes of performing repair procedures on multiple adjacent disk spaces due to the normal scoliotic curvature of the spine.

US Pat. App. 2005/0149026 to Butler et al., entitled Static and Dynamic Cervical Plate Constructs, published Jul. 7, 2005, describes an implanted cervical bone plate having a graft window located between the bone screw holes for the purposes of providing visualization and access to an intervertebral implant. The device described is applied after the intervertebral space has been repaired and after the implant has been positioned. The specification states specifically that an appropriately "sized dynamic plate is placed over the inserted bone implant"; thereafter the bone plate is located with respect to the implant by viewing the implant through the graft window and secured in place using bone screws.

Additional bone plate devices are disclosed in U.S. Pat. No. 3,741,205 to Markolf et al, and US Pat. Apps. 2005/0149026 to Butler et al. and 2007/0233107 to Zielinski.

There remains a need for and advantage to a permanently implantable spinal repair system and related method whereby the implant may be clearly viewed through the vertebral plate both inter-operatively and post-operatively. There is also a need for new systems and methods wherein the intervertebral implant and the bone screws used to secure the plate to the vertebrae can be prevented from backing out from the vertebrae in a quick and effective manner.

SUMMARY OF THE DISCLOSURE

The invention relates generally to systems and methods for securing adjacent vertebrae in a fixed spacial relationship. In one embodiment, the system includes at least one interbody repair implant, at least one implantable vertebral frame and at least one retention member. In this embodiment, the interbody repair implant is sized to fit in an intervertebral space. The at least one implantable vertebral frame is configured to span between the adjacent vertebrae. The frame is also configured to attach to each of the adjacent vertebra to postoperatively maintain a desired spatial relationship between the vertebrae. The frame has at least one internal aperture there-through for providing visual access to at least a portion of the interbody repair implant, both intra-operatively and post-operatively. The aperture is sized to have a smaller medio-lateral width than that of the interbody repair implant. The at least one retention member is attachable to the frame to cover at least a portion of the aperture. The retention member has a locking portion movable between an unlocked position and a locked position. In this embodiment, the locking portion prevents the retention member from being separated from the frame when in the locked position.

In some embodiments similar to the above embodiment, the locking portion includes at least one section that contacts a posterior side of the frame when the locking portion is in the locked position. The locking portion may include two sections that contact the posterior side of the frame on opposite sides of the aperture when the locking portion is in the locked position.

In some embodiments, the retention member includes at least one screw cover portion. The screw cover portion may cover at least part of a screw securing the frame to one of the adjacent vertebrae so as to prevent the screw from backing out of the vertebra. The retention member may include two, four, or more screw cover portions.

In some embodiments, the retention member includes a transitory locking portion having at least one resilient arm engageable with the frame for maintaining the retention member on the frame before the locking portion is moved from the unlocked position to the locked position.

In some embodiments, at least a portion of the retention member is radiolucent.

In some embodiments, the frame is configured to span between and remain postoperatively attached to at least three or at least four adjacent vertebrae. In these embodiments, the frame has at least two or at least three internal apertures there-through, respectively. Each aperture is configured to provide visual access to at least a portion of an interbody repair implant intra-operatively and post-operatively. In these embodiments, the system may include two or three retention members, respectively. Each retention member is attachable to the frame and is configured to cover at least a portion of one of the apertures. Each retention member has a locking portion movable between an unlocked position and a locked position. The locking portion in these embodiments prevents the retention member from being separated from the frame when in the locked position.

In some embodiments, the retention member is configured to provide visual, tactile and audible feedback when the locking portion is moved between the unlocked position and the locked position.

According to aspects of the invention, a method of fusing two or more adjacent vertebral bodies in a portion of a spinal column may be provided. In one such embodiment, the method includes the steps of inserting an interbody repair implant into a intervertebral space and securing an implantable vertebral fixation frame to the adjacent vertebral bodies over the implant. These steps are done such that a desired spatial relationship between the vertebrae is maintained. In this embodiment, the fixation frame has an internal aperture there-through for providing visual access to at least a portion of the interbody repair implant intra-operatively and post-operatively. The aperture is sized to have a smaller medio-lateral width than that of the interbody repair implant. This method further includes the steps of installing a retention member to the frame to cover at least a portion of the aperture, and moving a locking portion of the retention member from an unlocked position to a locked position. This locking of the retention member prevents the retention member from being separated from the frame.

In some embodiments similar to the above method, the locking portion includes at least one section that contacts a posterior side of the frame when the locking portion is in the locked position. The retention member may further include at least one screw cover portion, wherein the screw cover portion covers at least part of a screw securing the frame to one of the adjacent vertebrae. The screw cover portion prevents the screw from backing out of the vertebra. In some embodiments, there are two, four, or more screw cover portions.

In some embodiments, the retention member includes a transitory locking portion having at least one resilient arm that engages with the frame and maintains the retention member on the frame between the installing and moving steps. The method may include the step of observing the interbody repair implant with postoperative imaging through the retention member.

In some embodiments, the securing step involves securing the implantable vertebral fixation frame to at least three adjacent vertebral bodies to maintain a desired spatial relationship between the at least three vertebral bodies. The installing and moving steps may each be performed on more than one retention member. In some inventive methods disclosed herein, the retention member is configured to provide visual, tactile and audible feedback during the moving step.

DETAILED DESCRIPTION

Figure 1:
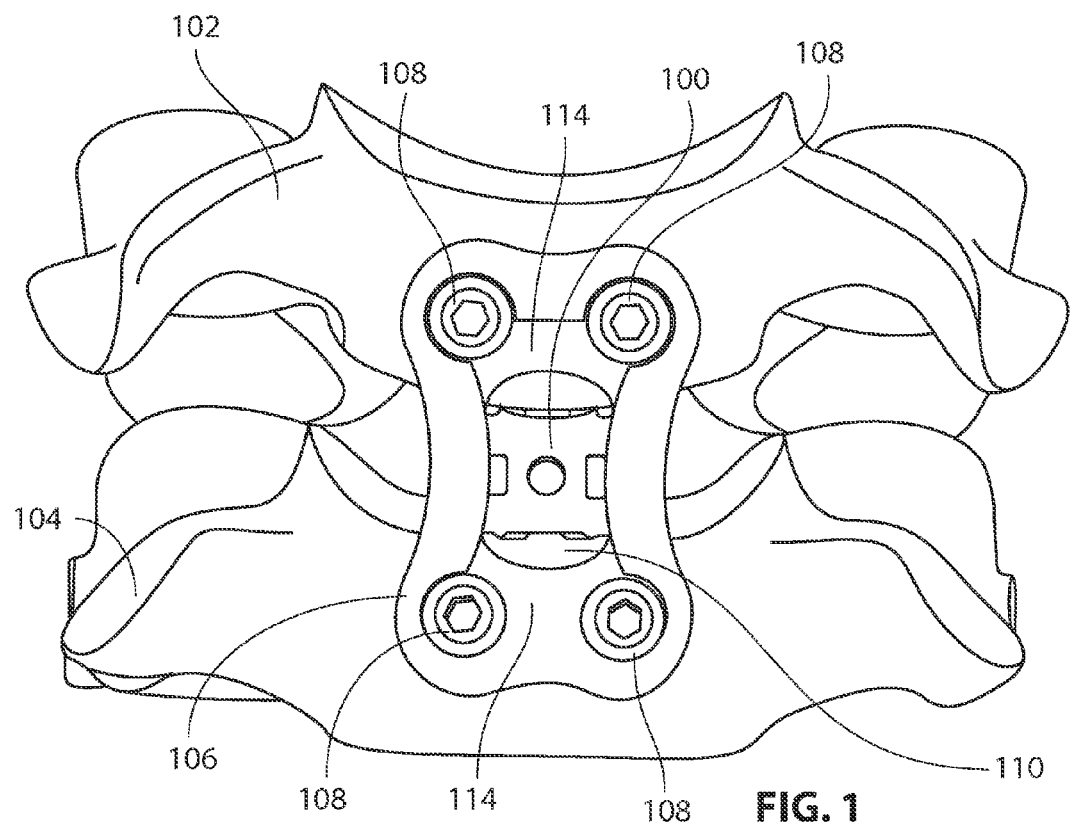
FIG. 1 is an anterior plan view showing an exemplary interbody repair device implanted in an intervertebral space and covered by an implantable vertebral frame secured between two adjacent vertebrae according to aspects of the present invention.
Figure 2:
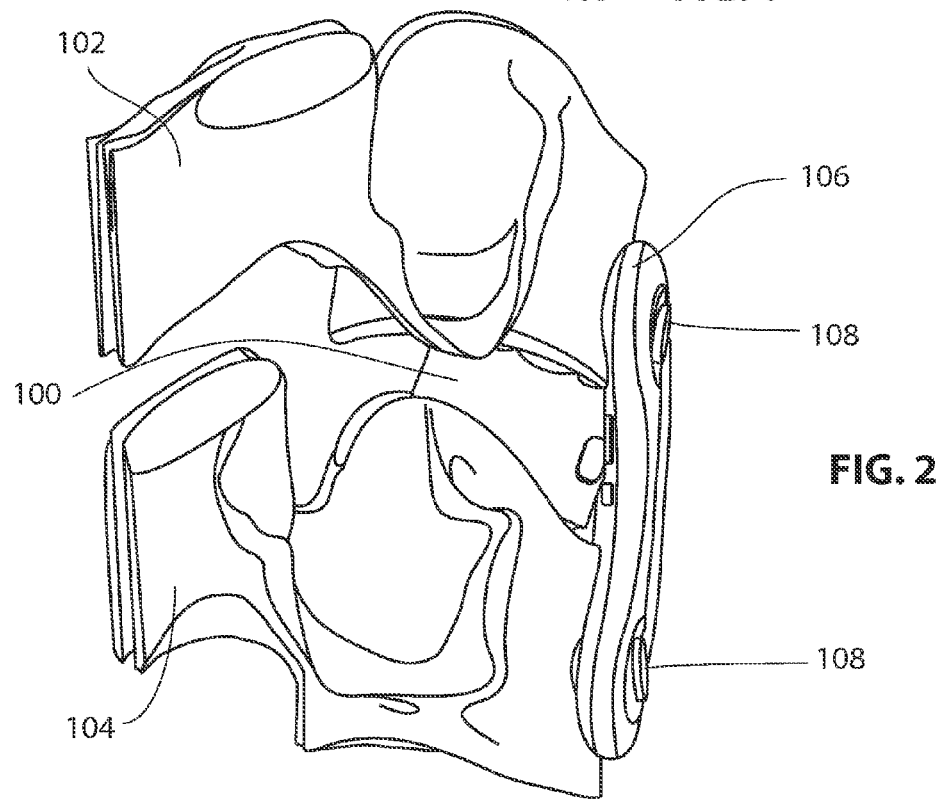
FIG. 2 is a lateral view showing the repair device and vertebral frame of FIG. 1.

FIGS. 1 and 2 show portions of an exemplary system constructed according to aspects of the present invention for securing adjacent vertebrae. Such systems are particularly useful for plating anterior surfaces of vertebral bodies of the cervical portion of the human spine, such as for treating compressions of the spine. Additional background and details of tools and surgical procedures associated with these systems can be found in U.S. patent application Ser. No. 12/616,762 entitled "Implantable Vertebral Frame Systems and Related Methods for Spinal Repair", filed Nov. 11, 2009.

The exemplary single-level system includes an interbody repair device 100 implanted in an intervertebral space between adjacent vertebral bodies 102 and 104. In some embodiments, the opposing endplates of adjacent vertebral bodies 102 and 104 are at least partially removed to prepare the intervertebral space to receive repair device 100. Device 100 may be configured to facilitate the fusion of vertebral bodies 102 and 104.

The exemplary system of FIGS. 1 and 2 also includes an implantable vertebral frame 106 configured to span between vertebral bodies 102 and 104. Two bone screws 108 may be used to rigidly secure frame 106 to each of the vertebral bodies 102 and 104. In this embodiment, frame 106 is secured to the anterior faces of vertebral bodies 102 and 104 along the medial centerline of the spine. The combination of repair device 100 and vertebral frame 106 may be used to permanently secure vertebral bodies 102 and 104 in a desired position relative to each other, such as for fusing the vertebral bodies together.

As shown, frame 106 may be provided with an aperture 110 there-through. Aperture 110 may be used to view aspects of repair device 100, such as its position, during surgery. After surgery, the aperture may be useful in viewing the development of bony ingrowth from the vertebral bodies 102 and 104 into repair device 100, as will be described further below. In some embodiments, the cranio-caudal dimension of aperture 110 is large enough to view a portion of each vertebral body where it contacts repair device 100, as shown. In some embodiments, aperture 110 is sized to have a smaller medio-lateral width than that of the repair device 100. Such an arrangement can allow frame 106 to assist in keeping repair device 100 from migrating in an anterior direction out of the intervertebral space.

Figure 3:
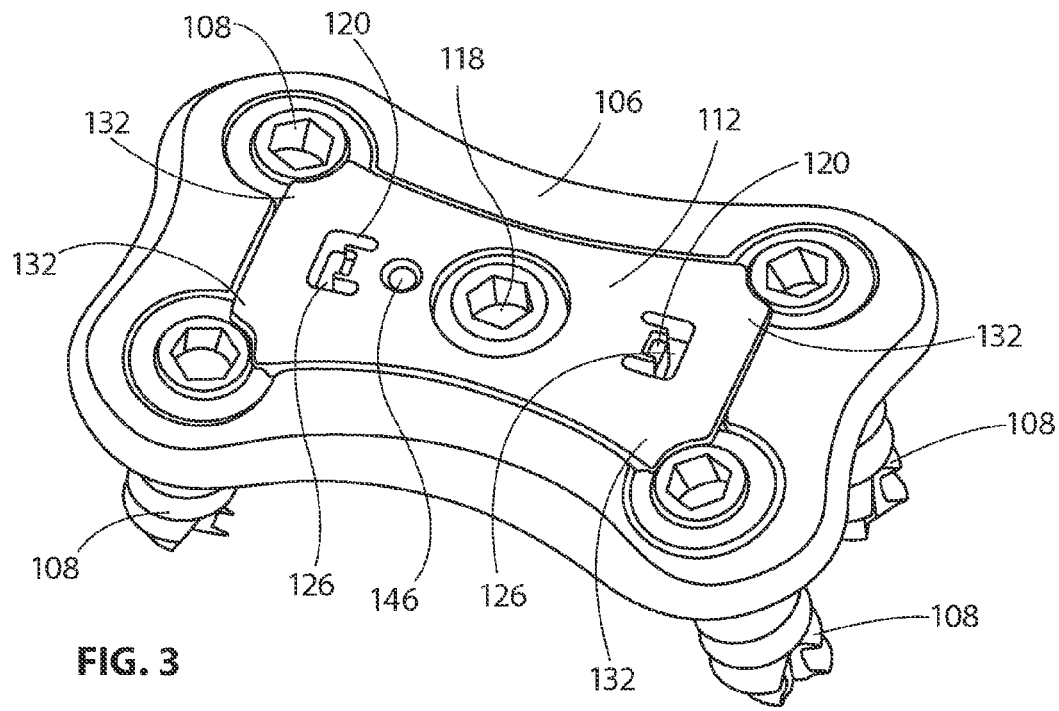
FIG. 3 is a perspective view showing the top of the repair device of FIG. 1 with an exemplary retention member installed.
Figure 4:
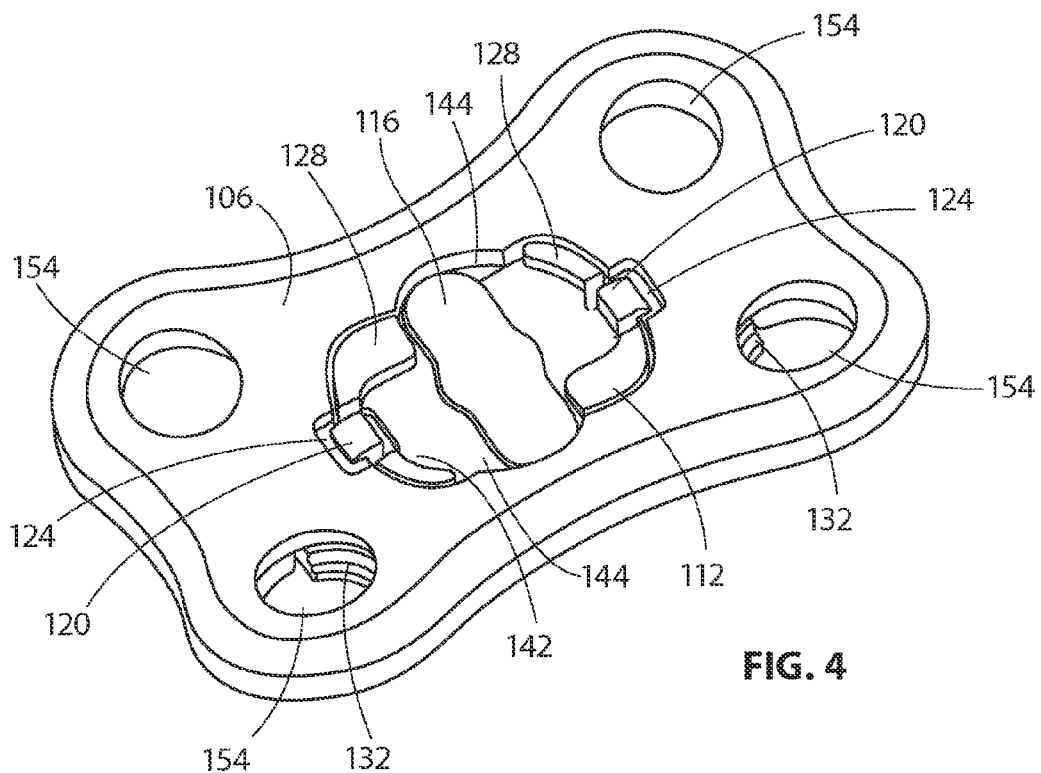
FIG. 4 is a perspective view of the bottom side of the repair device and retention member of FIG. 3.

FIGS. 3 and 4 show a retention member 112 attached to vertebral frame 106 and locked in place. In this embodiment, much of the anterior-posterior thickness of retention member 112 is received within a complementary-shaped recess 114 (shown in FIG. 1) in the anterior face of frame 106. This arrangement provides a generally smooth outer contour when retention member 112 is coupled to frame 106. Retention member 112 may cover aperture 110 as shown. In some embodiments, retention member 112 may serve to help retain repair device 100 in place. In some embodiments, retention member 112 serves to lock screws 108 in place as shown, as will be described in more detail below.

As seen in FIG. 4, retention member 112 may include a movable locking arm 116 on its posterior side for locking retention member 112 to frame 106. In this embodiment, locking arm 116 is operated by inserting a tool (not shown) in a keyed recess 118 on the anterior side of retention member 112 (shown in FIG. 3) and rotating locking arm 116 from an unlocked cranio-caudal orientation to a locked medio-lateral orientation, shown in FIG. 4. Retention member 112 may also include a transitory locking feature such as one or more resilient arms 120 engageable with frame 106. The transitory locking feature maintains retention member 112 on frame 106 before the locking arm 116 is moved from its unlocked position to its locked position. The construction and operation of these locking features are described in more detail below.

Figure 5:
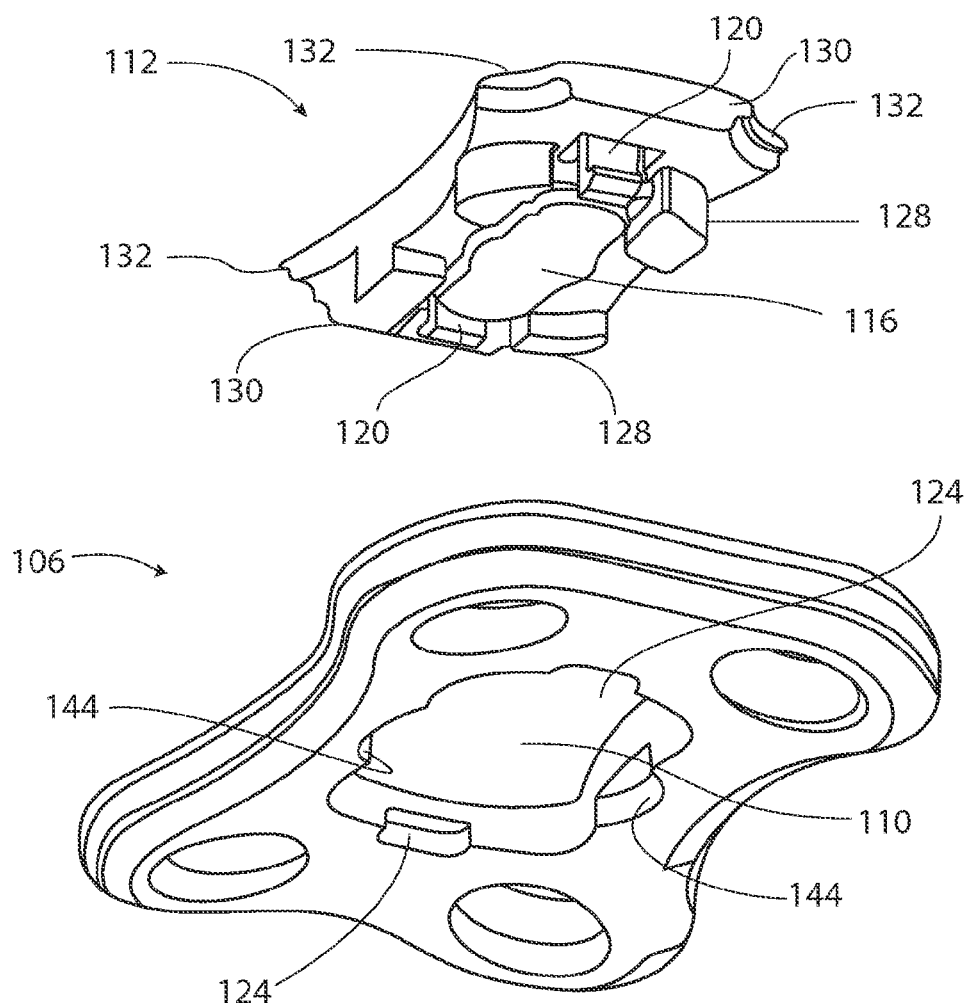
FIG. 5 is an exploded perspective view showing the repair device and retention member of FIGS. 3 and 4.
Figure 6:
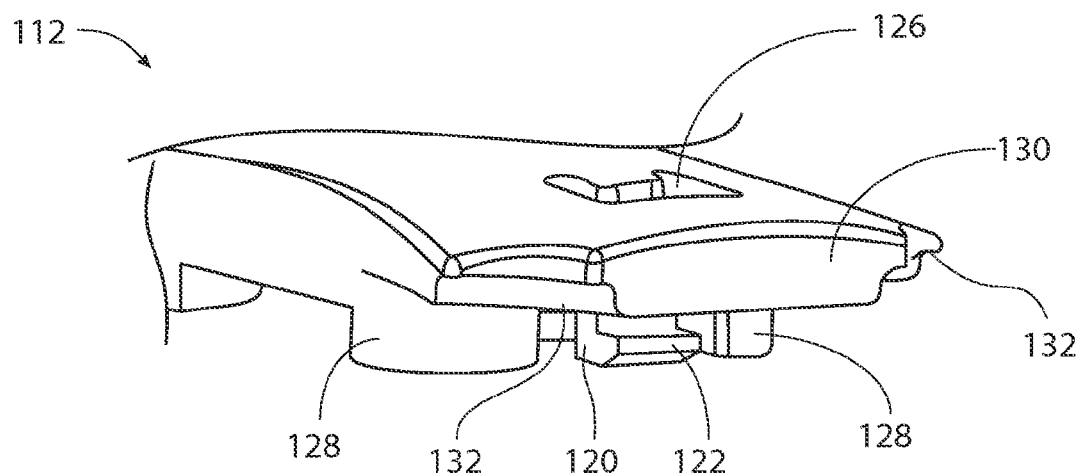
FIG. 6 is an enlarged perspective view showing an end portion of the exemplary retention member.

Referring to FIG. 5, vertebral frame 106 and retention member 112 are shown separated from each other and from the bottom (posterior) side. Retention member 112 is shown with locking arm 116 in the unlocked position. In this embodiment, retention member 112 is provided with a pair of resilient arms 120 downwardly depending from near each longitudinal end of the retention member. Each arm 120 is L-shaped and has a flange 122 projecting outwardly from its distal end, as best seen in FIG. 6. Inwardly facing, complementary-shaped recesses 124 may be formed in opposite longitudinal ends of aperture 110 of frame 106 for receiving the projecting flanges 122. Retention member 112 may be assembled to frame 106 from above by pressing it down over aperture 110. Beveled leading edges on flanges 122 cause resilient arm 120 to flex inwardly as they come into contact with the opposite sides of aperture 110. Once retention member 112 is fully received within aperture 110 and recess 114 (shown in FIG. 1), resilient arms 120 snap back to urge flanges 122 into recesses 124, thereby holding retention member 112 in place before locking arm 116 is actuated. With locking arm 116 in the unlocked position, retention member 112 can be removed from frame 106, such as by inserting a probe or other instrument into one or both of the pockets 125 formed in the anterior aspect of resilient arms 120 (best seen in FIG. 7), and applying a force to disengage resilient arms 120 from frame 106. This can be done interoperatively or during a subsequent revision procedure. A tool may also be inserted into pockets 125 and/or slots 126 surrounding the resilient arms 120 to grasp retention member 112 for removal and/or insertion.

As can be seen in FIGS. 5 and 6, in this embodiment retention member has a lower portion 128 that fits within aperture 110 of frame 106, and a larger flange portion 130 that resides above aperture 110 when coupled to frame 106. Retention member 112 may be provided with one, two, three, four, or more screw cover portions. In this exemplary embodiment, retention member 112 is provided with four screw cover portions 132, one located at each corner of the retention member. As best seen in FIGS. 5 and 6, each screw cover portion 132 is curved and has a notch for receiving a portion of the head of a screw 108. This arrangement prevents the screws 108 from backing out of the vertebrae once they are installed and retention member 112 is locked in place. FIG. 3 shows the inter-engagement between screw cover portions 132 and screws 108.

Figure 7:
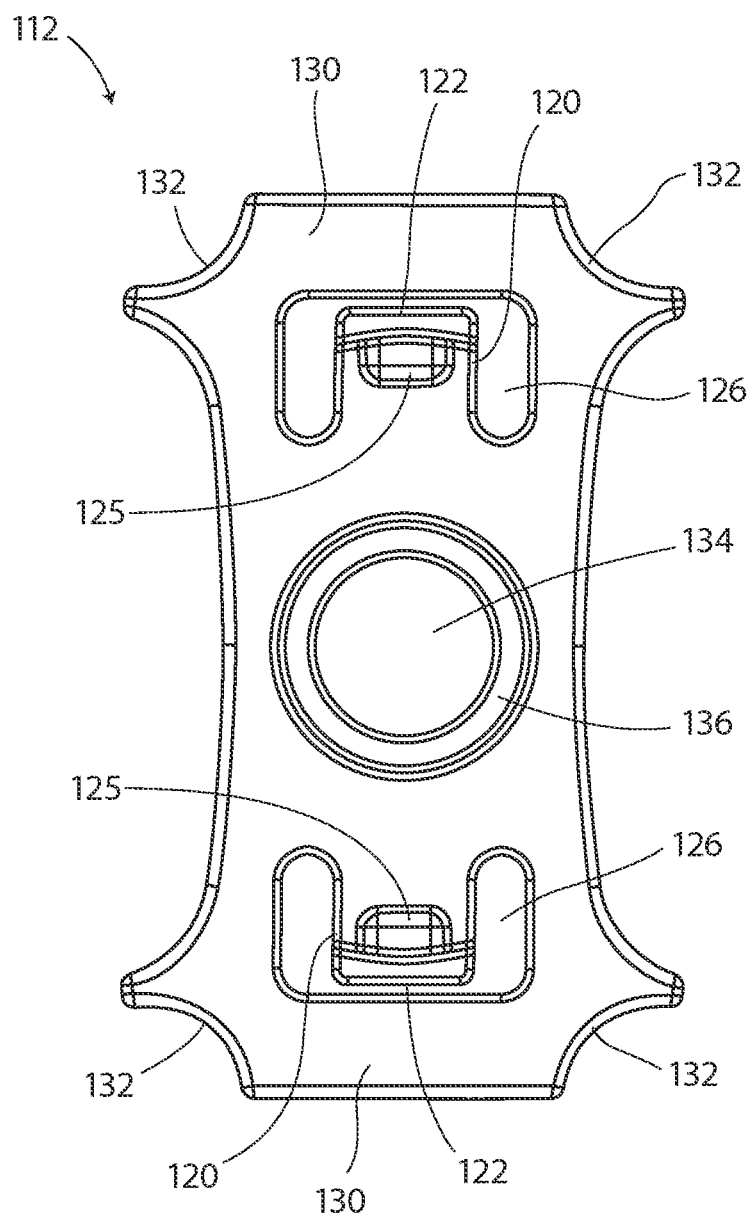
FIG. 7 is a top plan view showing the exemplary retention member with its locking arm removed for clarity.

FIG. 7 shows the top or anterior side of the exemplary retention member 112. The locking arm and keyed recess assembly is omitted from this view for clarity. As shown, a central hole 134 and counterbore 136 may be provided in the center of retention member 112 for receiving the locking arm and keyed recess assembly, as will be later described. Counterbore 136 allows the assembly to be recessed within retention member 112.

Figure 8:
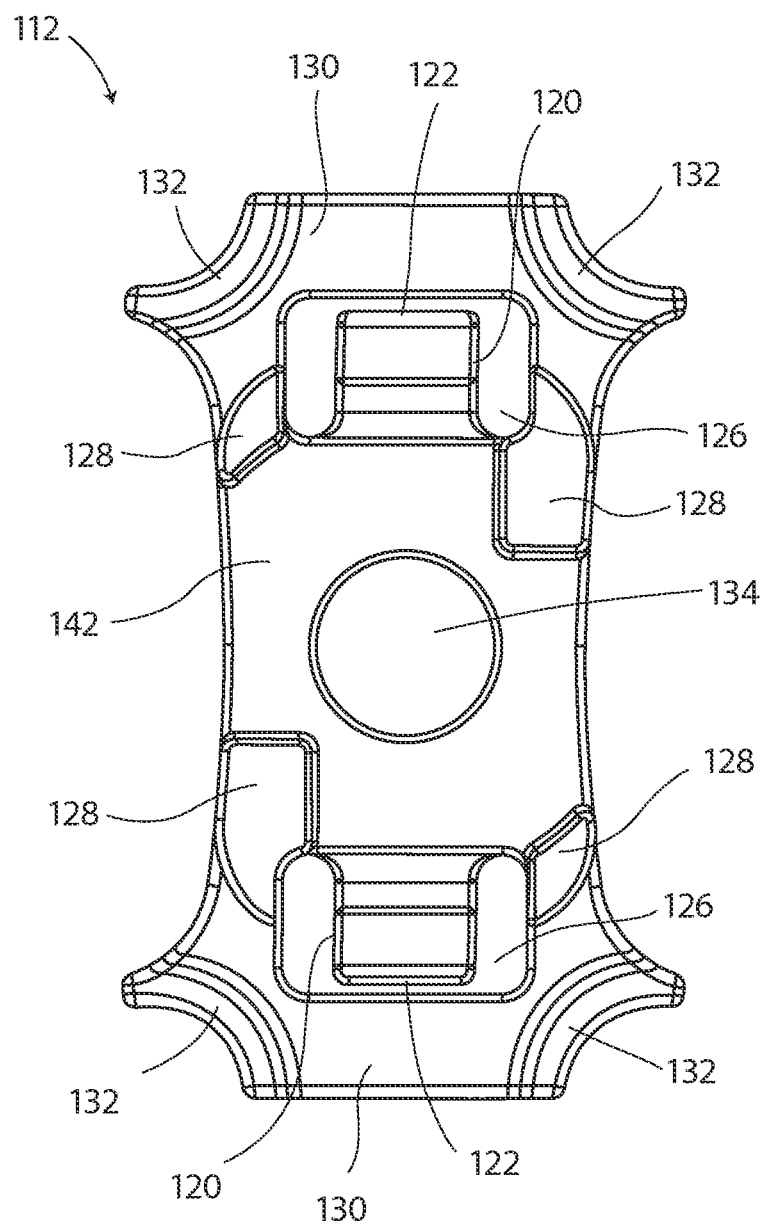
FIG. 8 is a bottom view showing the exemplary retention member with its locking arm removed for clarity.

FIG. 8 shows the bottom or posterior side of the exemplary retention member 112. The locking arm and keyed recess assembly is again omitted from this view for clarity.

Figure 9:
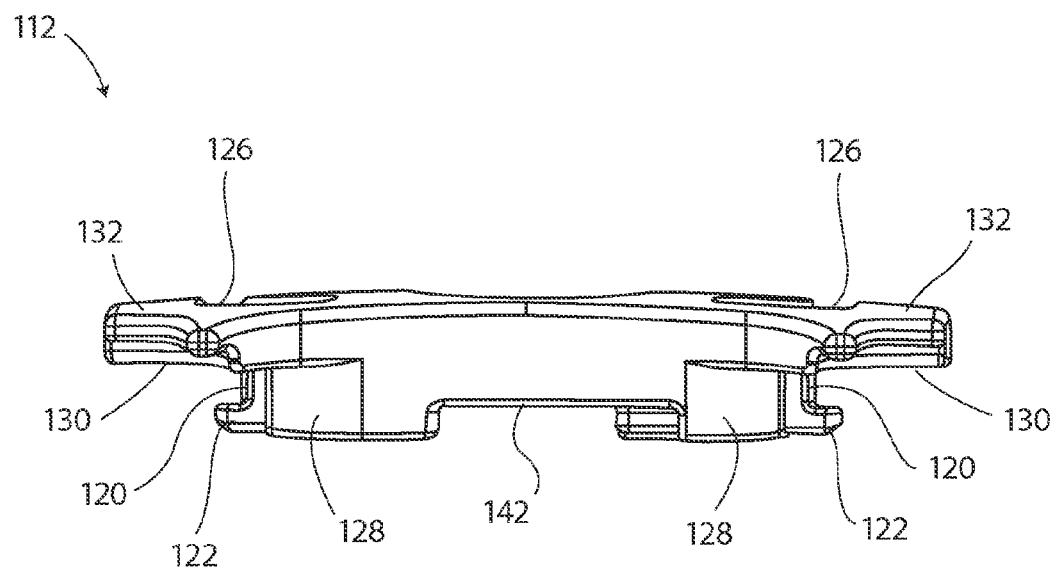
FIG. 9 is a side view showing the exemplary retention member with its locking arm removed for clarity.

FIG. 9 shows a side or lateral view of the exemplary retention member 112. The locking arm and keyed recess assembly is again omitted from this view for clarity.

Figure 10:
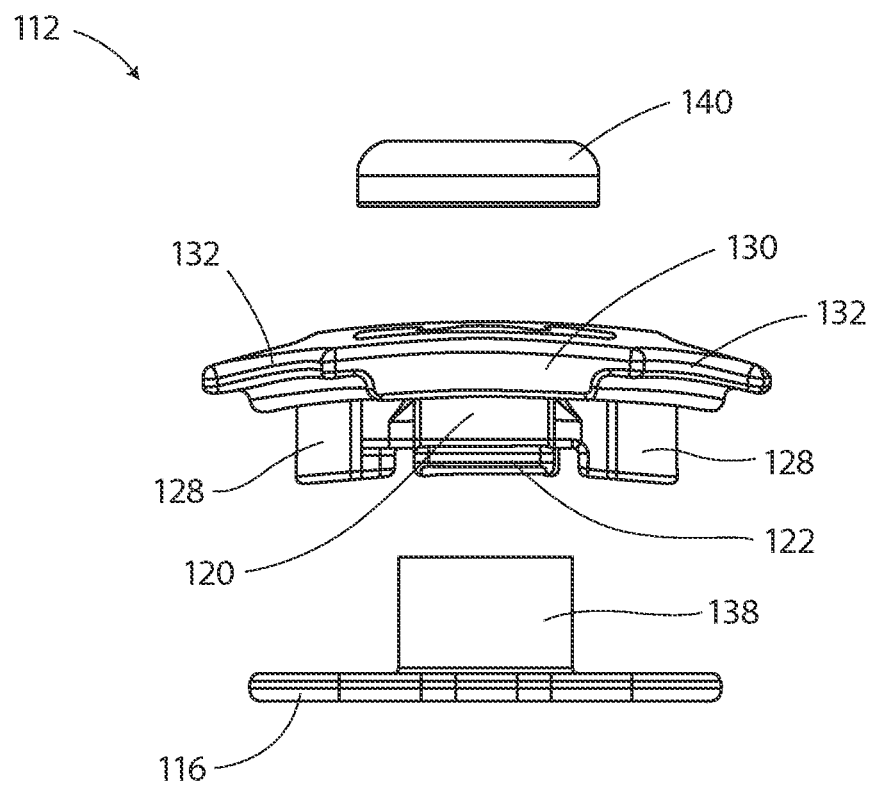
FIG. 10 is an exploded end view showing the exemplary retention member with its locking arm disassembled.

FIG. 10 shows an end or cranio-caudal view of the exemplary retention member 112. The locking arm and keyed recess assembly is shown with components in an exploded fashion for clarity. Locking arm 116 may be formed on or otherwise rigidly coupled to a cylindrical boss 138. In this embodiment, boss 138 has a keyed recess 118 (shown in FIG. 3) formed through its top surface. Boss 138 is configured to be rotatably received through the bottom side of central hole 134 within retention member 112. Cap ring 140 may be threaded, press-fit, welded, swaged or otherwise attached around the top of boss 138. This arrangement sandwiches the bottom of counterbore 136 between locking arm 116 and cap ring 140, thereby captivating the locking arm assembly on retention member 112 and allowing locking arm 116 to rotate relative thereto. Locking arm 116 is configured to slide along bottom surface 142, which is shown in FIGS. 8 and 9. As can be appreciated by viewing the configuration of the four portions 128 that depend from bottom surface 142 shown in FIG. 8, the locking arm may be oriented along the longitudinal (craniocaudal axis) of retention member 112 in an unlocked position, or it may be rotated 90 degrees counter-clockwise (when viewed from below as in FIG. 8) to a locked position. As shown in FIG. 10, locking arm 116 has a length that is longer than the width of the lower portion 128 of retention member 112. As such, the tips of locking arm 116 will extend beyond the bottom surface 142 of retention member 112 when in the locked position, and into recesses 144 formed in the bottom of frame 106, as shown in FIG. 4. In this locked position, retention member 112 is securely coupled to frame 106 and bone screws 108 (shown in FIG. 3) are prevented from backing out.

Figure 12:
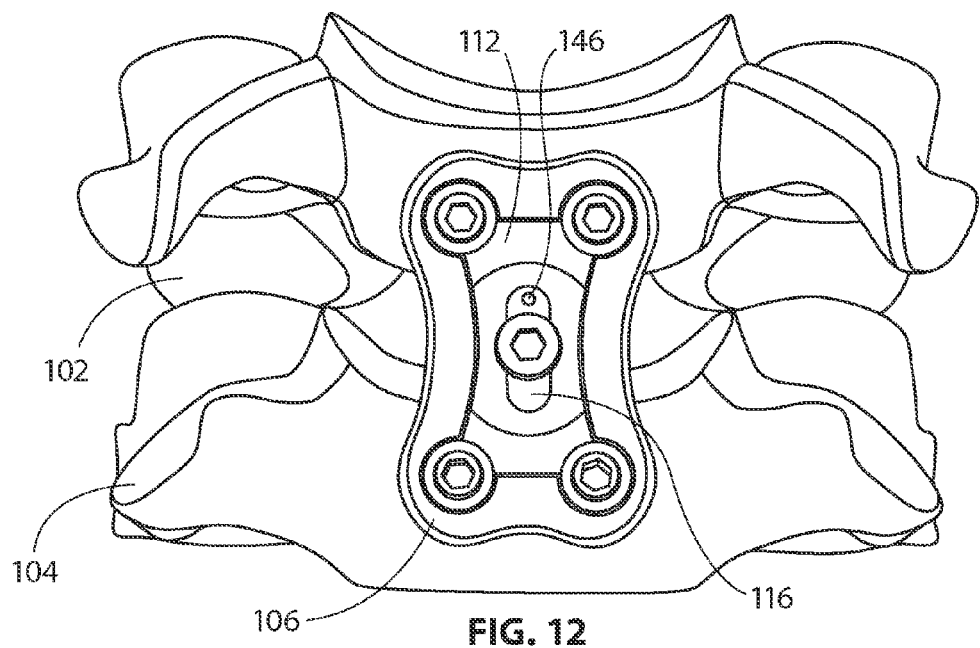
FIG. 12 is an anterior view depicting a retention member (semi-transparent for clarity) attached to a vertebral frame and in an unlocked position.
Figure 13:
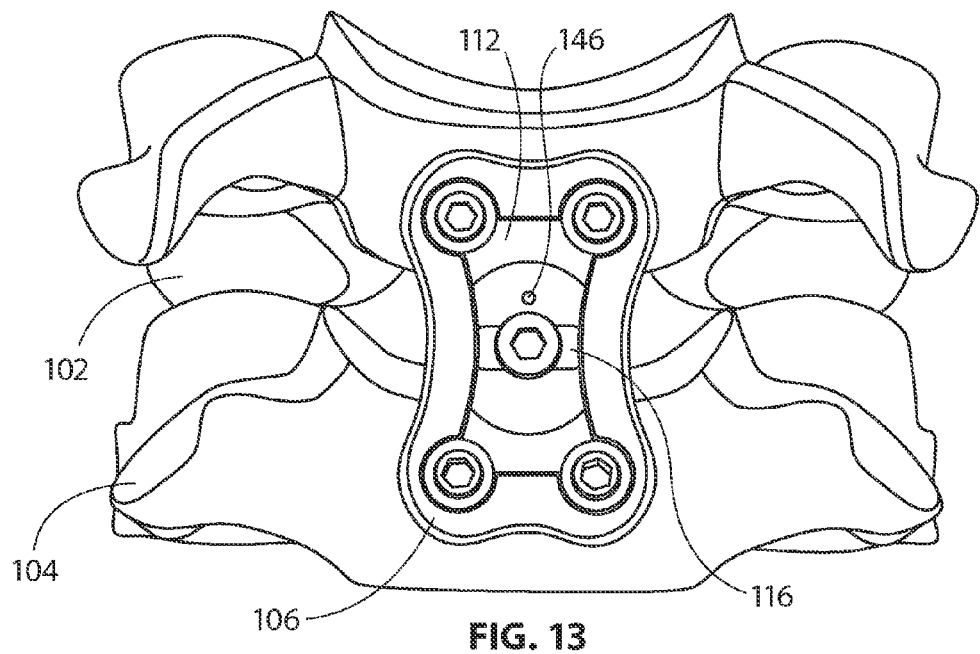
FIG. 13 is an anterior view depicting a retention member (semi-transparent for clarity) attached to a vertebral frame and in a locked position.

FIGS. 12 and 13 show retention member 112 coupled to vertebral frame 106 from an anterior view to further illustrate the locking of retention member 112 to frame 106. In both figures, the retention member 112 is shown as being semi-transparent for clarity. FIG. 12 shows locking arm 116 in an unlocked position, while FIG. 13 shows it turned 90 degrees in a clockwise direction to a locked position. According to aspects of the invention, at least one hole 146 may be provided through retention member 112 to align with locking arm 116 when it is either in the unlocked position (as shown in FIG. 12), or when it is in the locked position (not shown). Locking arm 116 may have a brightly colored dot on its surface to line up with hole 146, or locking arm 116 may be made from or coated with a brightly colored material. With this arrangement, a surgeon can clearly see whether locking arm 116 is in the unlocked position (or locked position). A detent feature (not shown) can be provided between locking arm 116 and retention member 112 to provide tactile feedback to a surgeon when locking arm 116 enters a locked position. The detent feature or a similar feature can also be configured to provide audible feedback to a surgeon. Thus, in some embodiments of the invention, a surgeon is provided with visual, tactile and audible feedback when locking arm 116 is moved between the unlocked position and the locked position. In other embodiments, only two, one, or none of these feedback features is provided.

Figure 11A:
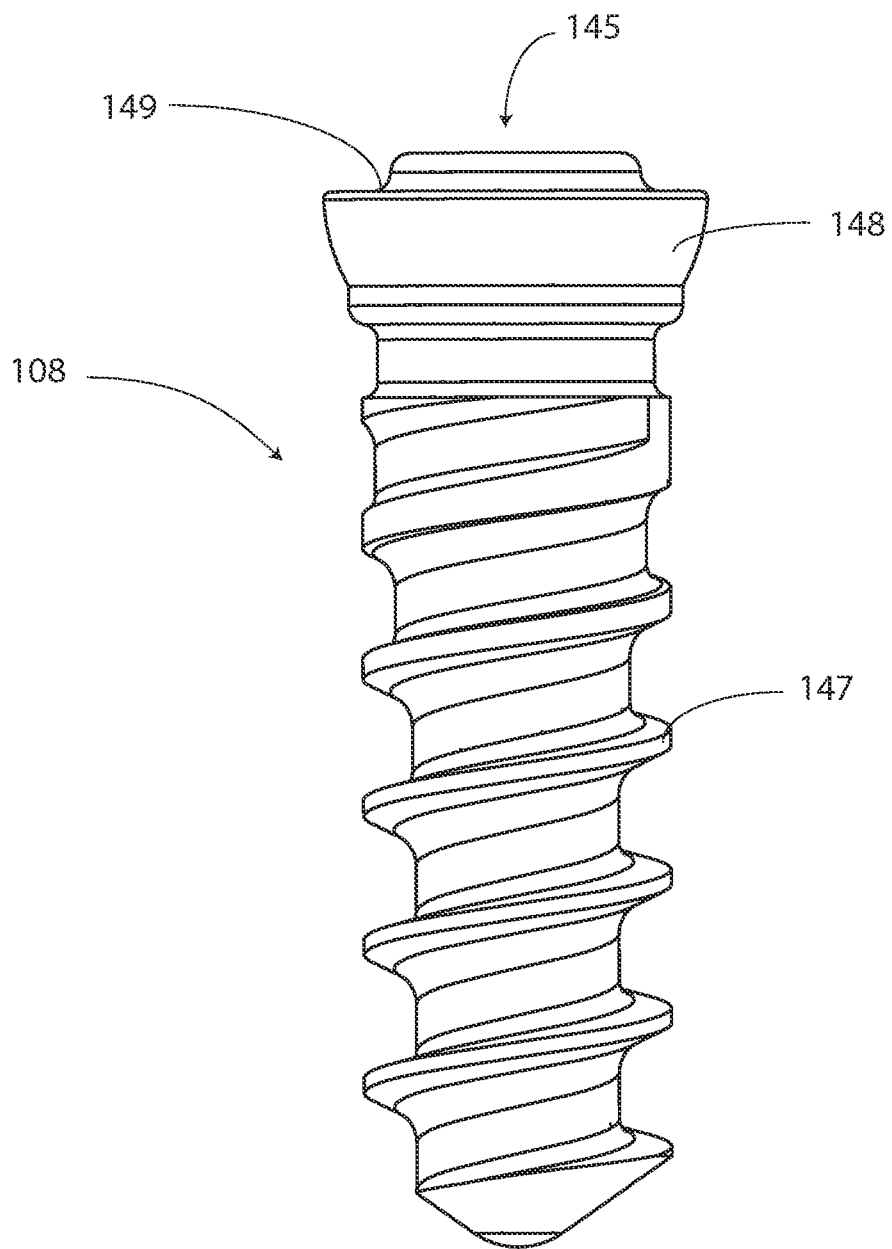
FIG. 11A is an exemplary bone screw for use in securing the vertebral frame to adjacent vertebrae.
Figure 11B:
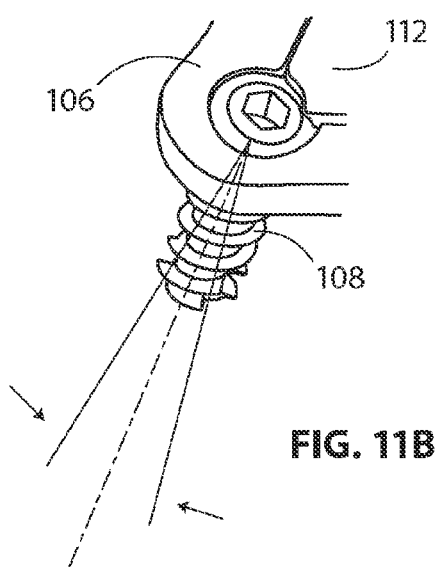
FIG. 11B is a perspective view showing the bone screw of FIG. 11A installed in a vertebral frame.

Referring to FIG. 11A, a proprietary bone screw 108 may be used to secure vertebral frame 106 to the vertebrae it spans. Bone screw 108 includes a head 145 and a threaded shank 147. Threaded shank 147 may be configured to be self drilling and/or self tapping. Bone screw 108 may be provided with head relief portion 149 to cooperate with screw cover portions 132 of retention member 112, as previously described. Bone screw 108 may also include a shoulder portion 148. In some embodiments, shoulder portion 148 has a spherical contour as shown. This contour cooperates with a mating contour on the anterior side of screw holes 154 in frame 106. This arrangement allows screw 108 to be mounted into a vertebral body at a variable angle relative to frame 106, as depicted in FIG. 11B. In some embodiments, this variability is defined by a 14 degree included angle. In other embodiments, fixed angle screws are used, or a combination of fixed angle and variable angle screws may be used.

Figure 16:
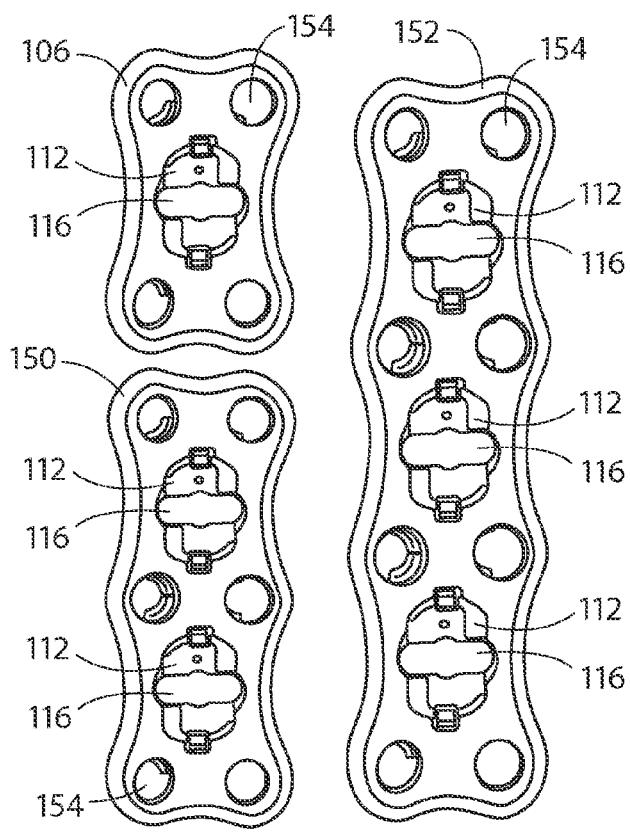
FIG. 16 is a bottom view showing the exemplary vertebral frames of FIGS. 3, 14 and 15.
Figure 14:
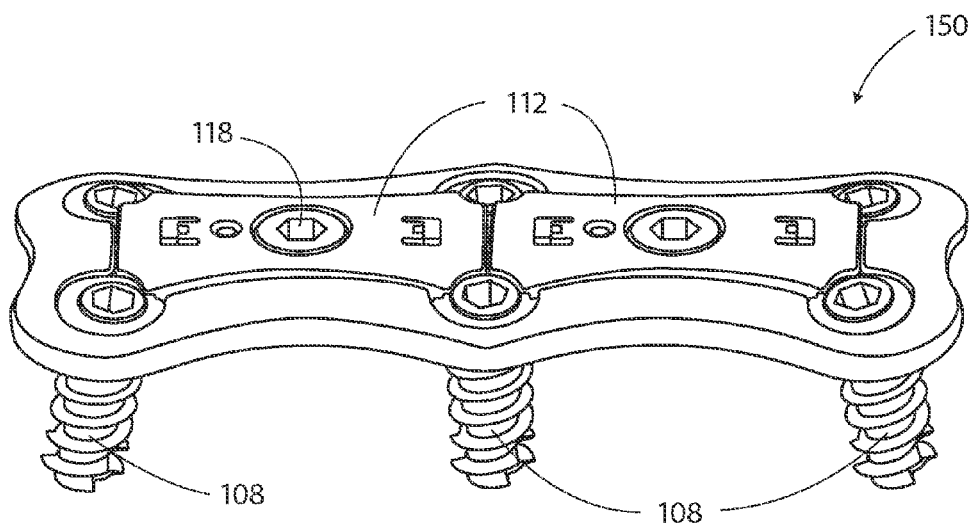
FIG. 14 is a perspective view showing an exemplary vertebral frame configured for spanning three adjacent vertebral bodies.
Figure 15:
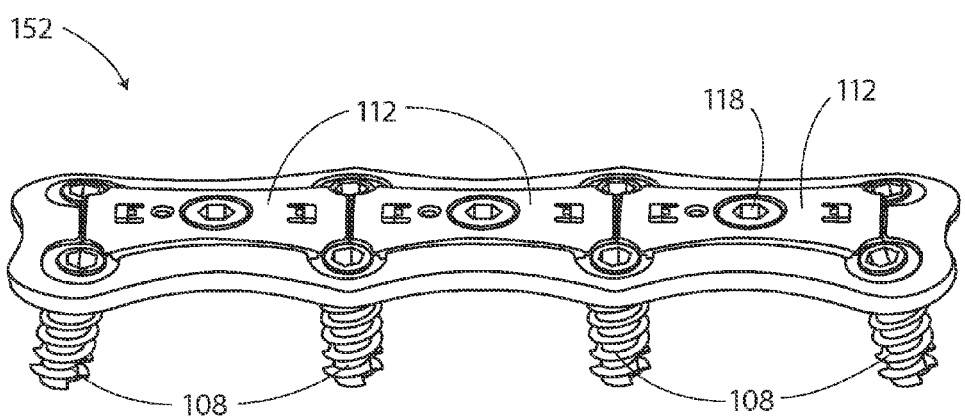
FIG. 15 is a perspective view showing an exemplary vertebral frame configured for spanning four adjacent vertebral bodies.

Referring to FIGS. 14-16, additional embodiments of the inventive vertebral frame and retainer member are shown. While the previously described frame 106 is configured to span two adjacent vertebral bodies (i.e. a single-level system), vertebral frame 150 shown in FIG. 14 is configured to span three adjacent vertebral bodies (i.e. a two-level system), and vertebral frame 152 shown in FIG. 15 is configured to span four adjacent vertebral bodies (i.e. a three-level system). The posterior side of all three vertebral frames 106, 150 and 152 and retention members 112 is shown in FIG. 16.

The construction and operation of multi-level vertebral frames 150 and 152 is similar to those of single-level frame 106. A repair implant similar to device 100 shown in FIGS. 1 and 2 may be implanted between each of the adjacent vertebrae connected by these multi-level frames. As with frame 106, a pair of holes 154 is provided through the frame in these exemplary multi-level embodiments to receive a pair of screws 108 for attaching the frame to each vertebral body. In the exemplary embodiments shown, multiple retention members 112 are used on each frame 150 and 152 to retain screws 108. Each retention member 112 secures four screws 108, with the middle screws each being retained by two retention members 112. Each retention member 112 may be symmetrical and identical, thereby allowing it to be put in any position on the frame and in either orientation. This arrangement reduces the part count in surgical kits containing one or more types of vertebral frames and simplifies the surgical procedures for implanting them. In other embodiments (not shown), a single retention member may be used. As previously described, each retention member may have a transitory locking portion having at least one resilient arm engageable with the frame for maintaining the retention member on the frame before a locking portion is moved from an unlocked position to a locked position.

Figure 17:
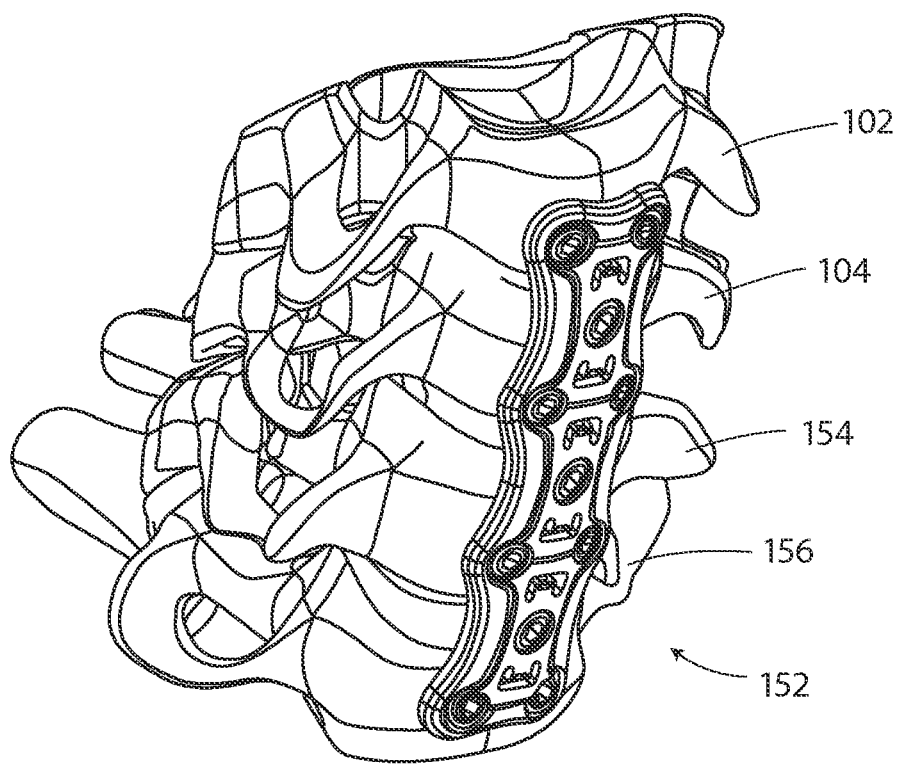
FIG. 17 is a perspective view showing the vertebral frame of FIG. 15 attached to four adjacent vertebral bodies.
Figure 18:
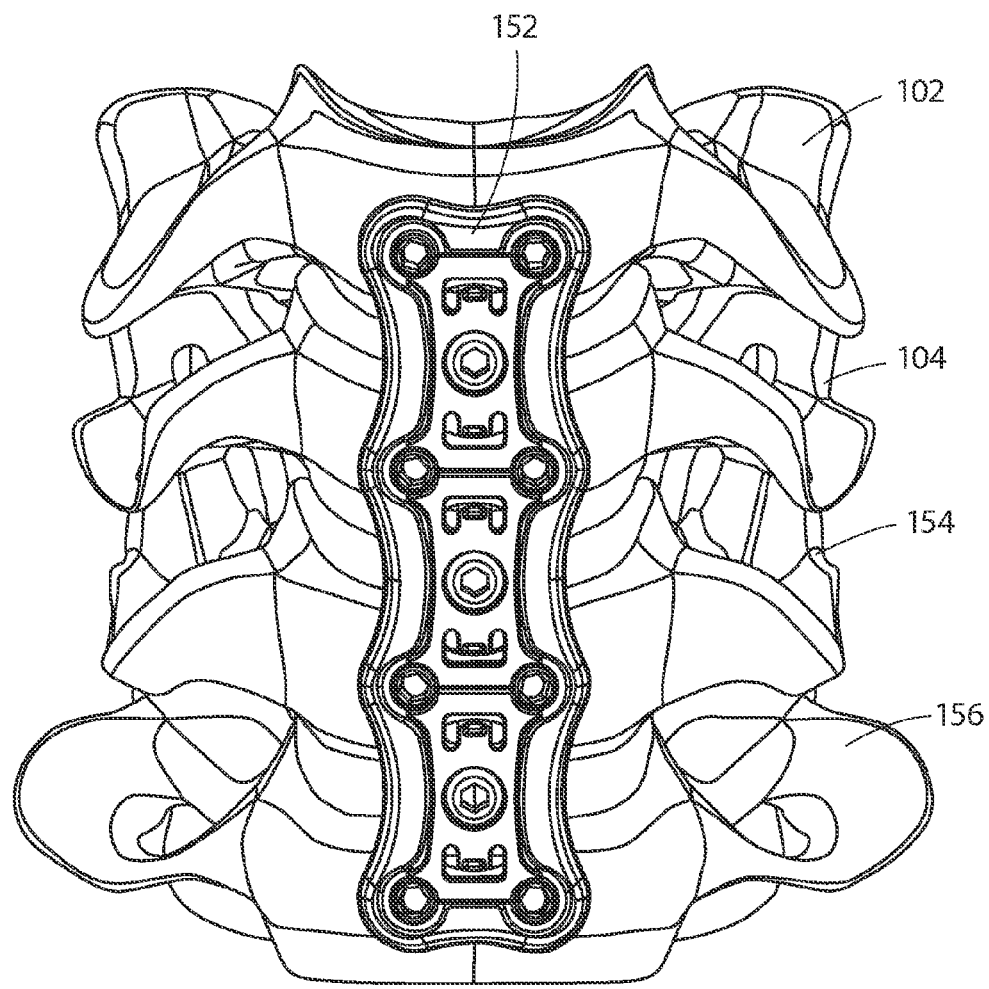
FIG. 18 is an anterior view showing the vertebral frame of FIG. 15 attached to four adjacent vertebral bodies.

FIGS. 17 and 18 show vertebral frame 152 implanted across four adjacent vertebral bodies 102, 104, 154 and 156.

Figure 19:
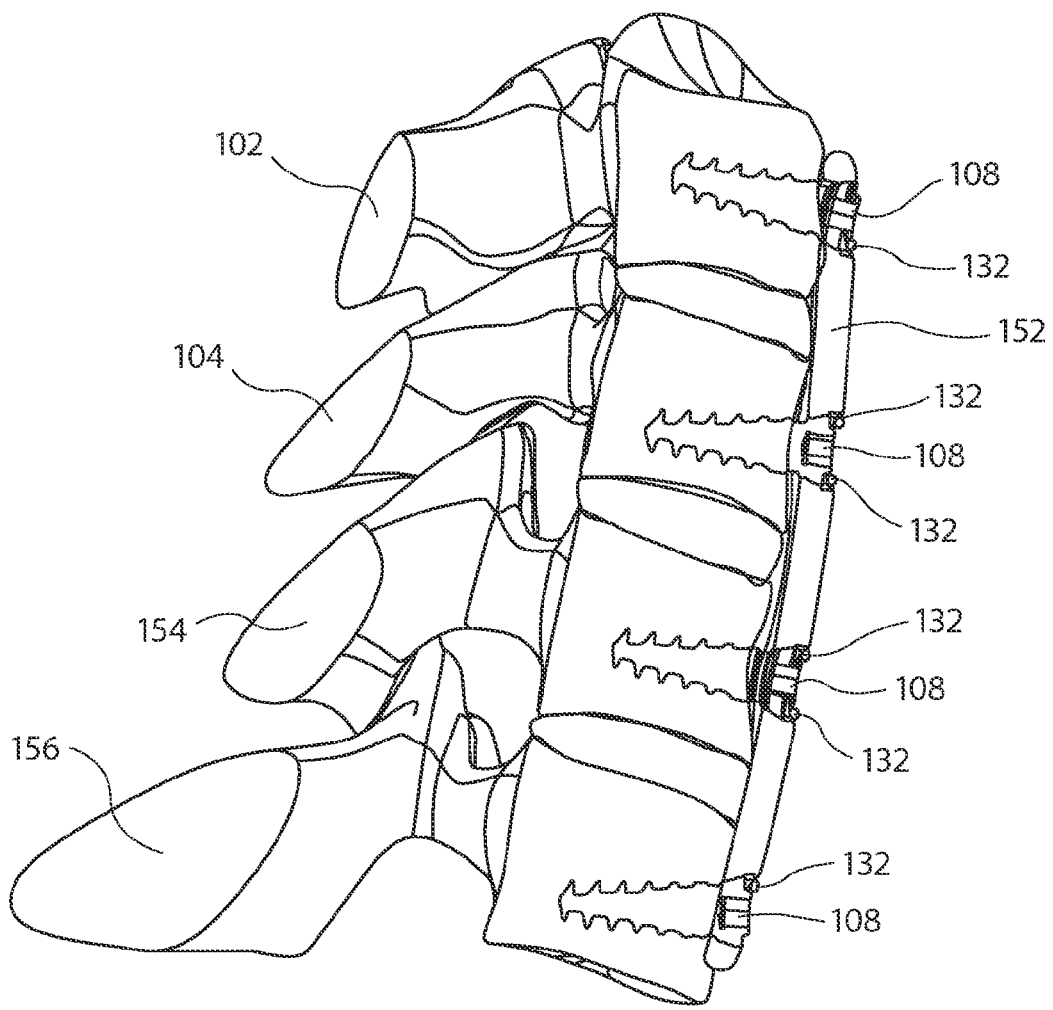
FIG. 19 is a lateral cross-sectional view showing the vertebral frame of FIG. 15 attached to four adjacent vertebral bodies.

FIG. 19 shows a medio-lateral looking cross-section of the vertebral frame 152 and adjacent vertebral bodies of FIGS. 17 and 18, taken along a cranio-caudal line running through the central axis of four screws 108 on one side of frame 152.

Figure 20:
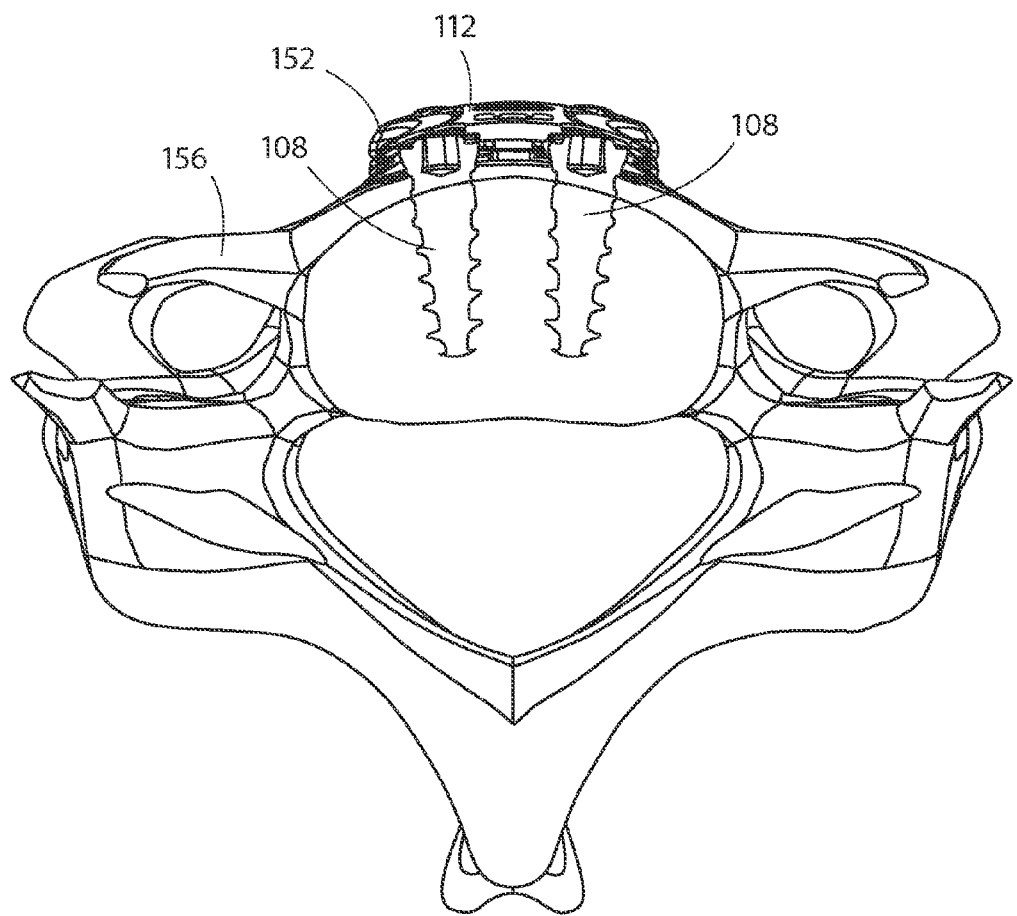
FIG. 20 is a cranio-caudal cross-sectional view showing the vertebral frame of FIG. 15 attached to a vertebral body.
Figure 21:
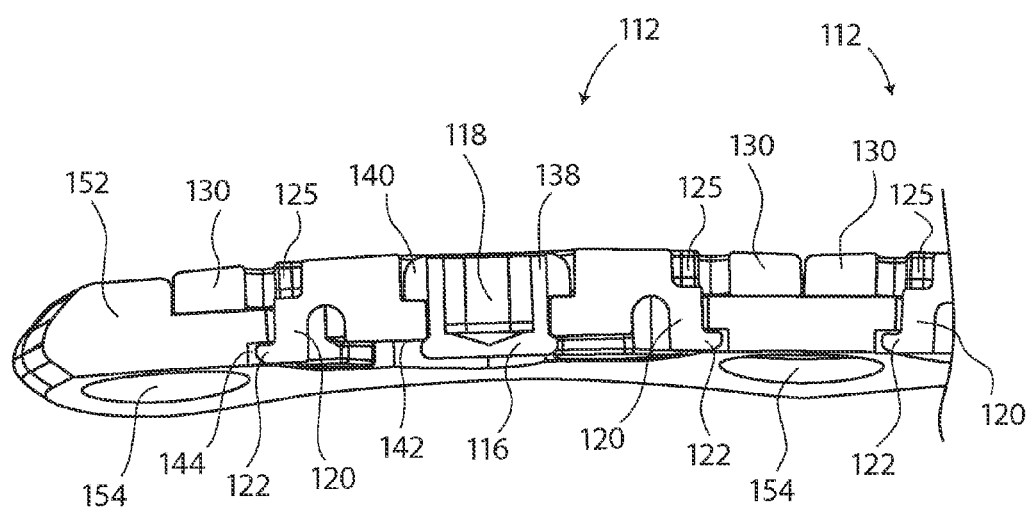
FIG. 21 is an enlarged lateral cross-sectional view showing a portion of the vertebral frame of FIG. 15.

FIG. 20 shows a cranio-caudal looking cross-section of a portion of vertebral frame 152 and a vertebral body of FIGS. 17 and 18, taken along a medio-lateral line running through the central axis of two adjacent screws 108 in a single vertebral body.

Aspects of the present invention can also be utilized to construct vertebral frames spanning more than four vertebral bodies.

According to aspects of the invention, the vertebral frames 106, 150 and 152 are configured to be low-profile for minimal interference with surrounding anatomy. In some embodiments, the vertebral frames are 2.1 mm at their thickest points. 1.2 mm leading and lateral edges may be provided as shown for easy insertion and in-situ adjustment. In some embodiments, the vertebral frames are 18 mm at their greatest width, and 13 mm at their narrowest width. The aperture(s) of each frame may be configured to be about 8 mm wide and about 12 mm long. The vertebral frames may have a pre-lordosed design as shown. Frames may be configured to allow translation up to about 1.5 mm per level. In some embodiments, the vertebral frames are made of titanium.

Surgical kits may be provided that include various sizes of vertebral frames. In some embodiments, the kits include single-level plates ranging from about 22 mm to about 34 mm long. In some embodiments, the kits include two-level plates ranging from about 36 mm to about 55 mm long. In some embodiments, the kits include three-level plates ranging from about 50 mm to about 77 mm long. In some embodiments, the kits include more than one type of vertebral frame. The kits may also include a range of self-drilling and self-tapping screws, fixed-angle screws, variable-angle screws, and recovery screws. In some embodiments, screws having a 4.0 mm nominal diameter are provided, and recovery screws having a 4.5 mm nominal diameter are also provided.

In some embodiments, retention member 112 is made of PEEK or another radiolucent material. This allows bone growth into an implant beneath retention member 112 to be viewed with various imaging techniques. Locking arm 116 may be made of titanium or another radio-opaque material so its locked status can be confirmed by imaging.

One exemplary method of installing a vertebral frame according to aspects of the invention is as follows. An incision is made and the anterior surfaces of the cervical vertebral bodies to be plated are exposed, as is well known in the art. The vertebral bodies may be distracted at this point to provide a desired spacial arrangement, to provide room to prepare the intervertebral space(s), and/or to insert the repair implant(s) 100. The intervertebral space(s) may be prepared, such as by removing at least portions of the disk annulus fibrosus, disk nucleus, and/or vertebral body endplates. The repair implant(s) may then be inserted between the adjacent vertebral bodies. Vertebral frame 106, 150 or 152 is then placed over the adjacent vertebral bodies covering the repair implant(s). The vertebral frame is typically placed on the anterior surfaces of the vertebral bodies along the medial centerline of the spine, and centered cranio-caudally over each repair implant 100. The aperture(s) 110 in the frame allow the surgeon to view the positioning of the implant(s) 100 during the procedure.

Once the vertebral frame 106, 150 or 152 is in the desired position on the vertebral bodies, it may be secured in place with bone screw 108. In the exemplary embodiments disclosed herein, two screws 108 are used for each vertebral body involved in the procedure. The screws may be self drilling and/or self tapping. Alternatively, holes may be pre-drilled in the bone before inserting the screws. The vertebral frame may be used as a drilling template, or a separate drilling template may be temporarily placed over the vertebral bodies for drilling prior to placement of the vertebral frame. In some embodiments, a separate drill guide may be attached to the drilling template or vertebral frame to aid in drilling and/or tapping.

Bone screws 108 are tightened, thereby securing vertebral frame 106, 150 or 152 to the vertebral bodies. The vertebral frame cooperates with repair implant(s) 100 to hold the vertebral bodies in the desired position postoperatively. Retention member(s) 112 may now be installed in the vertebral frame. As previously described, each retention member 112 may be placed over and partially into an aperture 110, and snapped into place by transitory locking features such as resilient arms 120 shown in FIG. 5. With a single 90 degree twist of each keyed recess 118 (shown in FIG. 3), the retention member 112 is locked into place by locking arm 116 (shown in FIG. 4), thereby fully securing implant 100 and four bone screws 108. As previously described, visual, tactile and audible feedback may be provided to the surgeon when the locking portion is moved between the unlocked position and the locked position. Each retention member 112 may be removed, if desired, by turning its keyed recess 118 in the opposite direction and prying the retention member 112 away from the frame against the force of the resilient arms 120. Once all retention members 112 are in place and locked, the plating procedure may be completed by closing the incision, as is well known in the art.

In some procedures it is desired that boney ingrowth from the vertebral bodies and/or bone growth material placed in repair implant(s) 100 allows the adjacent vertebral bodies to fuse together. Post-operative imaging can be used to monitor the progress of this healing process by viewing the implantto-vertebral body interfaces through the aperture(s) 110 of the vertebral frame 106, 150 or 152. This is enabled by the large viewing aperture(s) 110 provided by aspects of the present invention along with retention member(s) 112 being made from a radio-translucent material.

While inventive vertebral frame systems and associated methods have been described in some detail by way of illustration, such illustration is for purposes of clarity of understanding only. It will be readily apparent to those of ordinary skill and in the art in light of the teachings herein that certain changes and modifications may be made thereto without departing from the spirit and scope of the appended claims.

All publications and patent applications mentioned in this specification are herein incorporated by reference to the same extent as if each individual publication or patent application was specifically and individually indicated to be incorporated by reference.

What is claimed is:

1. A method of fusing two or more adjacent vertebral bodies in a portion of a spinal column, the method comprising:

inserting an interbody repair implant into an intervertebral space;

securing an implantable vertebral fixation frame to the adjacent vertebral bodies over the implant such that a desired spatial relationship between the vertebrae is maintained, the fixation frame having an internal aperture there-through for providing visual access to at least a portion of the interbody repair implant intra-operatively and post-operatively, the aperture sized to have a smaller medio-lateral width than that of the interbody repair implant;

visualizing the interbody repair implant through the aperture intra-operatively or post-operatively;

installing a retention member to the frame to cover at least a portion of the aperture;

after the installing step, moving a locking portion of the retention member from an unlocked position to a locked position to prevent the retention member from being separated from the frame, wherein the locking portion comprises at least one section that contacts a posterior side of the frame when the locking portion is in the locked position; and wherein the step of moving a locking portion of the retention member comprises rotating an elongated locking arm that is elongated along a first axis around a second axis transverse to the first axis.

2. The method of claim 1 wherein the retention member further comprises at least one screw cover portion, wherein the screw cover portion covers at least part of a screw securing the frame to one of the adjacent vertebrae, the screw cover portion preventing the screw from backing out of the vertebra.

3. The method of claim 2 wherein the retention member further comprises two screw cover portions.

4. The method of claim 2 wherein the retention member further comprises four screw cover portions.

5. The method of claim 1 wherein the retention member further comprises a transitory locking portion having at least one resilient arm that engages with the frame and maintains the retention member on the frame between the installing and moving steps.

6. The method of claim 1 further comprising the step of observing the interbody repair implant with postoperative imaging through the retention member.

7. The method of claim 1 wherein the securing step involves securing the implantable vertebral fixation frame to at least three adjacent vertebral bodies to maintain a desired spatial relationship between the at least three vertebral bodies.

8. The method of claim 7 wherein the installing and moving steps are each performed on more than one retention member.

9. The method of claim 1 wherein the retention member is configured to provide visual, tactile and audible feedback during the moving step.

10. The method of claim 1 wherein the locking arm is located on a posterior side of the retention member.

11. The method of claim 1 wherein the locking arm has exactly two sections that contact the posterior side of the frame when the locking portion is in the locked position.

12. The method of claim 11 wherein the two sections of the locking arm each contact a recess located in the posterior side of the frame.

13. The method of claim 1 wherein the locking portion of the retention member does not contact a posterior side of the frame when the locking portion is in the unlocked position, and wherein the locking portion is retained by the retention member when in the unlocked position.

* * * * *